(12) United States Patent
Gadde

(10) Patent No.: US 11,700,977 B2
(45) Date of Patent: Jul. 18, 2023

(54) AUTOMATIC SYSTEM FOR PROVIDING FULL BODY SHOWER TO A USER

(71) Applicant: Pardha S. Gadde, London (GB)

(72) Inventor: Pardha S. Gadde, London (GB)

( * ) Notice: Subject to any disclaimer, the term of this patent is extended or adjusted under 35 U.S.C. 154(b) by 0 days.

(21) Appl. No.: 17/804,097

(22) Filed: May 26, 2022

(65) Prior Publication Data

US 2022/0279985 A1 Sep. 8, 2022

Related U.S. Application Data

(63) Continuation-in-part of application No. 16/729,582, filed on Dec. 30, 2019, now Pat. No. 11,375,857.

(51) Int. Cl.
| | |
|---|---|
| A47K 3/32 | (2006.01) |
| A47K 3/28 | (2006.01) |
| A47K 7/04 | (2006.01) |
| A47K 4/00 | (2006.01) |

(52) U.S. Cl.
CPC ............. *A47K 3/325* (2013.01); *A47K 3/285* (2013.01); *A47K 3/287* (2013.01); *A47K 4/00* (2013.01); *A47K 7/04* (2013.01)

(58) Field of Classification Search
CPC ........ A47K 3/325; A47K 3/285; A47K 3/287; A47K 4/00; A47K 7/04
USPC .................................... 4/597, 598, 606, 570
See application file for complete search history.

(56) References Cited

U.S. PATENT DOCUMENTS

| | | | | |
|---|---|---|---|---|
| 3,042,949 A | * | 7/1962 | Mosely | A47K 7/046 |
| | | | | 4/606 |
| 6,930,747 B2 | | 8/2005 | Lee | |
| 7,269,862 B2 | | 9/2007 | Rooke et al. | |
| 2006/0032439 A1 | * | 2/2006 | Burato | B05B 5/03 |
| | | | | 4/597 |
| 2018/0036200 A1 | * | 2/2018 | Wilkinson | A47K 10/48 |

FOREIGN PATENT DOCUMENTS

| | | | | |
|---|---|---|---|---|
| CN | 209235935 U | * | 8/2019 | |
| WO | WO-03017816 A1 | * | 3/2003 | ............... A47K 3/32 |

* cited by examiner

*Primary Examiner* — Tuan N Nguyen
(74) *Attorney, Agent, or Firm* — Willie Jacques; Emanus, LLC

(57) ABSTRACT

An automatic system for providing full body shower with round the body cleaning to a user is illustrated. The automatic system includes a solid supporting unit with horizontal and vertical frames. A primary cleaning unit and a secondary cleaning unit are provided for the cleaning of the head portion and the body surface of a user. The first horizontal frame and the secondary cleaning unit are configured with vertical upward and downward movement along the vertical frame using an elevating means. Each of the primary and secondary cleaning units comprises a plurality of nozzles, brushes and ultraviolet (UV) light sources. An air dryer chamber propelling dry air for drying the wet body and head portion of the user is utilized. The automatic shower system can also be used in the horizontal orientation.

20 Claims, 17 Drawing Sheets

AUTOMATIC SYSTEM FOR PROVIDING FULL BODY SHOWER TO A USER

CROSS-REFERENCE TO THE RELATED APPLICATION(S)

The application is continuation-in-part of U.S. patent application Ser. No. 16/729,582 filed on 30 Dec. 2019 which claims the benefit of, and priority to, U.S. Provisional Patent Application Ser. No. 62/786,514 filed on filed 30 Dec. 2018 which is incorporated by reference herein in its entirety.

FIELD OF THE INVENTION

The subject matter of the instant invention relates generally to a shower system. Particularly and not exclusively, the subject matter of the instant invention relates to an energy efficient, time saving and water saving automatic shower system that provides full body shower to a user.

BACKGROUND OF THE INVENTION

It is a well-known fact that taking a bath or shower provides a plurality of health benefits including but not limited to enhancement of lung capacity, soothing spine, lightening the moods, supporting weak muscles of the limb, improving body's immunity, enabling secretion of hormones such as cortisol, beta-endorphin, or ACTH in balanced form, cleaning and hydrating eyes, hair and skin, regulating core body temperature, relief from headaches and migraines, regulating blood pressure, soothing sports related acnes, good sleep, tackling flu and coughs, loosing extra calories thereby maintaining right body mass index (BMI), providing proper warm-up before workout or exercise, enabling body cells to produce stress fighting chemicals and soothing itchy skin and rashes, to name a few.

The traditional way of taking bath using a bathtub provides the benefits of a relaxed mind and relief from stress including the relief from muscle pain and body aches. However, the disadvantages associated with a bathtub include the consumption of huge space and high cost for installation and ineffectiveness in rinsing the whole body. On the other hand, a shower enclosure comes with a plurality of advantages including consumption of less space, easy installation, low cost of installation and maintenance, quick and flexible time of bath/shower, and effective cleansing and rinsing of the body.

However, there are certain disadvantages associated with a traditional shower system. The first and foremost disadvantage includes a built-in model that cannot be customized according to individual user preferences. That is to say, the traditional shower system is not water efficient and energy efficient as the user has no control over the temperature of the water and also the flow of water. Further, many of the processes and procedures to be followed while taking a shower/bath in traditional shower systems consume much time. The operation of the traditional shower system is cumbersome. Further to this, each user irrespective of the age, gender and body constitution, maybe having his/her own specific requirements to be met while taking a shower which is not accessible in the traditional shower system.

Further disadvantage of the traditional shower system lies therein that the cleaning of the shower system progresses before the shower gets finished and before the user leaves from the place of the shower. This brings in and puts on the risk of the personal hygiene of the user by the bacteria, organic material and other risk causing elements that have not been removed from the shower system. Further to this, in many of the traditional shower systems, a user is required to dry his head and body on his/her own as there will not be any drying system provided therein to dry the wet head portion and body surface. Still further, there will an apparent wastage of soap or shampoo or lotion or any other cleaning agents used during the shower. Furthermore, in many of the traditional shower system designs and modules, the user is required to use his/her own brushes for cleaning the head portion and the body surface. Manual operation of the traditional shower system is found to be difficult, especially for elderly people, who can't move their hands, who can't bend whole body to clean lower or back part of the body or who can't move the neck due to neck injuries and also for those people who have partial or full paralysis and hospital patients.

As a remedy to the aforementioned disadvantages, an automatic shower has been provided as a solution that provides for a hygienic and an indolence shower experience to a user from the beginning to end. Accordingly, in order to overcome the shortcomings of the prior art, there is strong felt a need an energy efficient, time saving and water saving automatic system to facilitate full body shower to a user with the implementation of 360° round the body cleaning to the user and characterized by:

- compactness in size and configuration;
- portability;
- facilitation of full body shower to all users including users with limited or differential mobility;
- additional cleaning and drying facility including a plurality of automatic dispensers;
- facilitation of both vertical and horizontal washing;
- enhancement of the personal hygiene of the user;
- the usage of the ultraviolet light source as a disinfectant for the user and the system;
- at least one sensor unit to detect the presence and to identify the positioning of the vertical objects including human beings;
- automatic switching ON/OFF based on the input received from the sensors provided therein including the detection of the presence and identification of the position of the user inside the system;
- facilitation of auxiliary positioning unit for the right positioning of vertical objects including patients, old age people and persons with limited motional ability;
- a display unit to display a plurality of attributes of the functional elements and enable the user to control a plurality of functional elements of the automatic shower system; and,
- enablement of the user to control a plurality of attributes including but not limited to temperature of the water, the flow rate of water, the flow of dry air, vertical and horizontal movement of the system according to user requirement and duration of the functioning of the system.

OBJECTS OF THE INVENTION

Objects of the instant invention are as stated below:

An object of the instant invention is to provide an energy efficient, time saving and water saving automatic shower system that facilitates full body shower to a user in which 360° round the body cleaning is provided to the user;

Another object of the instant invention is to provide an automatic shower system that facilitates full body shower to a user in which 360° round the body cleaning is facilitated all users including a user with limited or differential mobility;

An additional object of the instant invention is to provide an automatic shower system that facilitates full body shower to a user which is compact in size and configuration, and which is enabled with portability;

Yet another object of the instant invention is to provide an automatic shower system that facilitates full body shower to a user in which an additional cleaning and drying facility is included with a plurality of automatic dispensers;

A further object of the instant invention is to provide an automatic shower system that facilitates full body shower to a user in which the system can be used as both vertical as well as horizontal shower orientation;

Furthermore object of the instant invention is to provide an automatic system that facilitates full body shower to a user in which the system enhances the personal hygiene of a user;

Yet another object of the instant invention is to provide an automatic system that facilitates full body shower to a user in which an ultraviolet light source is used as a disinfectant for the user and the shower system;

A further object of the instant invention is to provide an automatic system that facilitates full body shower to a user in which at least one sensor is provided to detect the presence and to identify the positioning of the user inside the system;

Still further object of the instant invention is to provide an automatic shower system that facilitates full body shower to a user in which the system is automatically switched ON/OFF based on the input received from the sensor provided therein;

Furthermore object of the instant invention is to provide an automatic shower system that facilitates full body shower to a user in which an auxiliary positioning unit is provided for the right positioning of users, patients, old age people and persons with limited or differential mobility inside the system;

Another object of the instant invention is to provide an automatic system that facilitates full body shower to a user in which the display unit is provided display a plurality of attributes of the functional elements and enables the user to control a plurality of functional elements of the system; and, Yet another object of the instant invention is to provide an automatic system that facilitates full body shower to a user in which the user is enabled to control a plurality of attributes of the system including but not limited to temperature of water, flow rate of water and duration of the functioning of the system.

Other objects, aspects, features, and goals of the instant invention appear in the following description and the appended claims and will be clearer when reading with reference to the accompanying drawings.

SUMMARY OF THE INVENTION

The instant invention provides an energy-efficient, time-saving and water-saving automatic system that facilitates full body shower to a user wherein the system is configured to provide 360 degrees round the body cleaning to a user. The automatic system is compact in size and configuration, and further enabled with portability.

Principally, in accordance with the most preferred aspect of the instant invention, the automatic system as disclosed in the instant invention includes a solid supporting unit with a horizontal frame and a vertical frame. The horizontal frame extends from the top end of the vertical frame thereby making perpendicular orientation with respect to the vertical frame. The bottom end of the vertical frame is mounted on to the ground using a mounting means. There is provided a marked region in front of the mounting means wherein the user is required to stand to receive the full body shower.

Typically, in accordance with the most preferred aspect of the instant invention, there is provided at least one primary cleaning unit mounted onto the horizontal frame. The first mounting unit is a showerhead. The primary cleaning unit is adapted to clean the head portion of the user including the scalp hair. The primary cleaning unit is configured to have controlled and regulated vertical movement along the vertical frame with respect to the user standing within the marked region to facilitate the cleaning of the head portion of the user. Further, the primary cleaning unit is adapted to include a plurality of uniform nozzles, brushes and a plurality of ultraviolet (UV) light sources. Each such nozzle is adapted to dispense water including but not limited to dispense dry air, soap-water, medicament, serum, ointment, and moisturizer, etc. based on the user requirement onto the head portion of the user whereas each such brush is adapted to dispense soap-water onto the head portion of the user and further facilitate the rinsing of the head portion of the user. Each brush is further enabled to the scrubbing of the head portion of the user via a motion including a zigzag or back-forth movement, rotating, etc. A first elevating means is used to facilitate the controlled and regulated vertical movement of the horizontal frame in an upward and downward direction with the help of chain/thread/belt connected to up and down fixed pulleys working in conjunction with a motor along the vertical frame. There is provided a primary guides/tracks to enable the movement of the horizontal frame in the upward and downward direction.

Typically, in accordance with the most preferred aspect of the instant invention, there is provided at least one secondary cleaning unit in the form of a ring. The ring is including but not limited to a circular, or a semi-circular, or an elliptical, or a triangular, or a square, a hexagon or tubular shape ring. The secondary cleaning unit is positioned between the primary cleaning unit and the marked region. The secondary cleaning unit is operably coupled to the vertical frame of the supporting unit via a ring arm. The positioning of the secondary cleaning unit is made parallel to the horizontal frame of the supporting unit. The secondary cleaning unit is further configured to have controlled and regulated vertical movement along the vertical frame with respect to the user standing within the marked region to facilitate the cleaning of the body surface of the user. The secondary cleaning unit is adapted to include a plurality of uniform nozzles and brushes, and a plurality of ultraviolet (UV) light sources. Each such nozzle is adapted to dispense water including but not to dry air, soap-water, medicament, serum, ointment, and moisturizer, etc based on the user requirement onto the body surface of the user. Each such brush is adapted to dispense soap-water onto the body surface of the user and further facilitate the rinsing of the body surface of the user via a motion including a zigzag or back-forth movement, rotating, etc. A second elevating means is used to facilitate the controlled and regulated vertical movement of the secondary cleaning unit in an upward and downward direction with the help of a chain/thread/belt connected to up and down fixed pulleys working in conjunction with a motor along the vertical frame. There is provided a secondary guides/tracks to enable the movement of the at least one secondary cleaning unit in the upward and downward direction along the vertical frame. Further, the material of the brushes in the primary and secondary cleaning units is either a soft fabric, polymeric or a fiber or a micro-fiber.

Typically, in accordance with the most preferred aspect of the instant invention, the ultraviolet (UV) light sources used in the aforementioned primary and secondary cleaning units is a light-emitting diode [LED]. The ultraviolet (UV) light from the light-emitting diode [LED] is adapted to function as a disinfectant for the user and the shower system. Further, the shower system can be used without water and soap by adding UV Lights (Ultraviolet light) to the dryer ring to clean the germs on the body, this feature helpful for water scarcity places.

Typically, in accordance with the most preferred aspect of the instant invention, there is provided a waterproof main conduit. The main conduit includes a plurality of secondary conduits that are insulated from each other and made waterproof. The plurality of the secondary conduits and enabling the flow of water, soap-water, moisturizer, ointment, medicament, and serum, etc. to be used for the washing and cleaning of the user. Further the plurality of the secondary conduits enabling the flow of dry air for drying the head portion and the body surface of the user and receiving a plurality of electrical cables including the cables of said first and second elevating means.

Typically, in accordance with the most preferred aspect of the instant invention, there is provided an air dryer chamber. The air dryer chamber includes a heating element to heat the air received from an external source and thereby generates dry air. The generated dry air from the air dryer chamber is propelled to the primary and secondary cleaning units through the secondary conduits to facilitate the drying of the head portion and body surface of the user.

Typically, in accordance with the most preferred aspect of the instant invention, there is a main control unit adapted to control the functioning of a plurality of functional elements of the shower system including a plurality of sensors. That is to say, the main control unit is adapted to control the functioning of the primary and secondary cleaning units, the first and second elevating means, the ultra-violet (UV) light sources, the display unit, the sensor, the primary and secondary slots, and the air dryer chamber.

Further, in accordance with the most preferred aspect of the instant invention, there is a display unit adapted to display a plurality of attributes of the functional elements and enable the user to control a plurality of functional elements of the automatic shower system.

Typically, in accordance with the most preferred aspect of the instant invention, there is provided an auxiliary unit adapted to position the patients, old age people and persons with limited motional ability within the marked region. The system is further configured to automatically switch ON/OFF based on the input received from the plurality of sensors.

Further, according to another aspect of the instant invention, the shower system is having a plurality of secondary cleaning units wherein each secondary cleaning unit is acting as a separate unit for air dryer, water dispenser, soap-water dispenser, moisturizer dispenser, UV light sources, brushes, etc.

Furthermore, according to the most preferred aspect of the instant invention, the secondary cleaning unit is enabled with variable diameter to encompass the body of a thin or thick user and provided with an opening and closing means for entering and exiting the shower system.

Still further, according to the most preferred aspect of the instant invention, the automatic shower system can store the different parameters set by the user for different functional elements in a user's profile and allows the user to choose the same while using the system again.

The following description is illustrative in nature and is not intended to be in any way limiting. In addition to the illustrative aspects, embodiments, and features described above, further aspects, embodiments, and features will become apparent by reference to the following detailed description.

BRIEF DESCRIPTION OF THE ACCOMPANYING DRAWINGS

The accompanying drawings illustrate the best mode for carrying out the invention as presently contemplated and set forth hereinafter. The preferred embodiments of the instant invention will now be more particularly described, by way of example only, with reference to the accompanying drawings. The present invention may be more clearly understood from a consideration of the following detailed description of the preferred embodiments taken in conjunction with the accompanying drawings wherein like reference letters and numerals indicate the corresponding parts in various figures in the accompanying drawings, and in which:

DETAILED DESCRIPTION OF THE INVENTION

Figure 1:
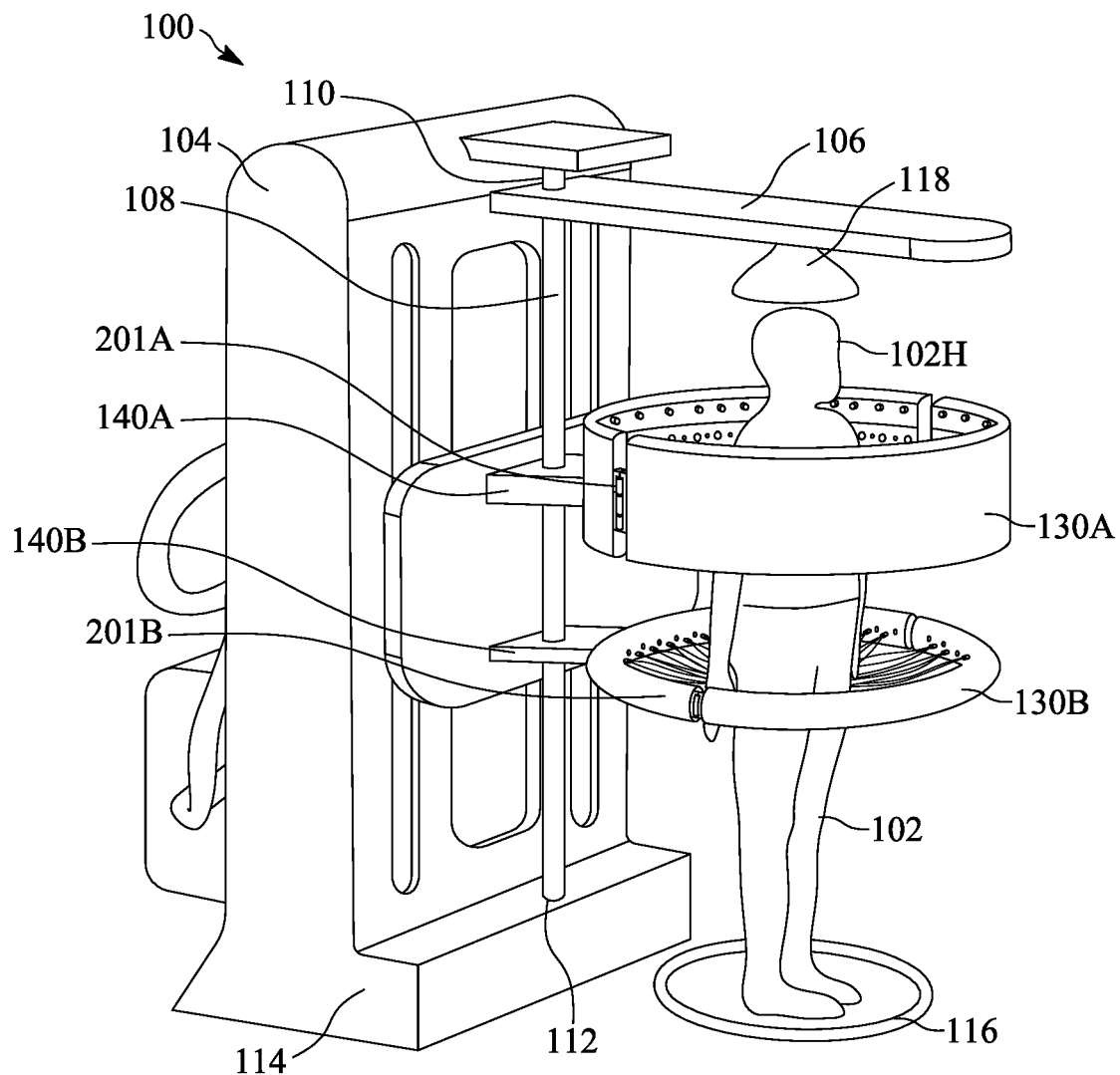
FIG. 1 is an illustration of an automatic shower system for providing full body shower to a user, in accordance with the most preferred embodiment of the instant invention.

In order to alleviate the drawbacks associated with one or more prior art disclosures, an automatic system for providing a full body shower to a user is exemplified and explained as herein.

Referring now from FIG. 1 to FIG. 4, an automatic system for providing full body shower to a user, in accordance with the most preferred embodiment of the instant invention, is illustrated. The automatic system 100 is adapted to provide round the body 360 0 cleaning to a user 102. The automatic system 100 comprises a solid supporting unit denoted by the reference numeral 104. The supporting unit 104 includes a horizontal frame 106 and a vertical frame 108. The horizontal frame 106 is configured to extend from the top end 110 of the vertical frame 108 thereby making perpendicular orientation with respect to the vertical frame 108. The bottom end 112 of the vertical frame 108 is mounted on to the ground using a mounting means 114. The mounting means 114 is any solid supporting base adapted to receive the supporting unit 104. There is a marked region 116 in front of the mounting means 114. The user 102 who wishes to take full body shower/bath/cleaning using the system 100 is required to stand within the marked region 116.

In accordance with the most preferred embodiment of the instant invention, there is provided at least one primary cleaning unit 118 which is mounted onto the horizontal frame 106. The primary cleaning unit 118 is adapted to clean the head portion 102 H including the scalp hair of the user 102. The primary cleaning unit 118, in usual practice, is a showerhead. The primary cleaning unit 118 is configured for the controlled and regulated vertical movement along the vertical frame 108 with respect to the user 102 standing within the marked region 116 to facilitate the cleaning of the head portion 102 H of the user 102.

Figure 3:
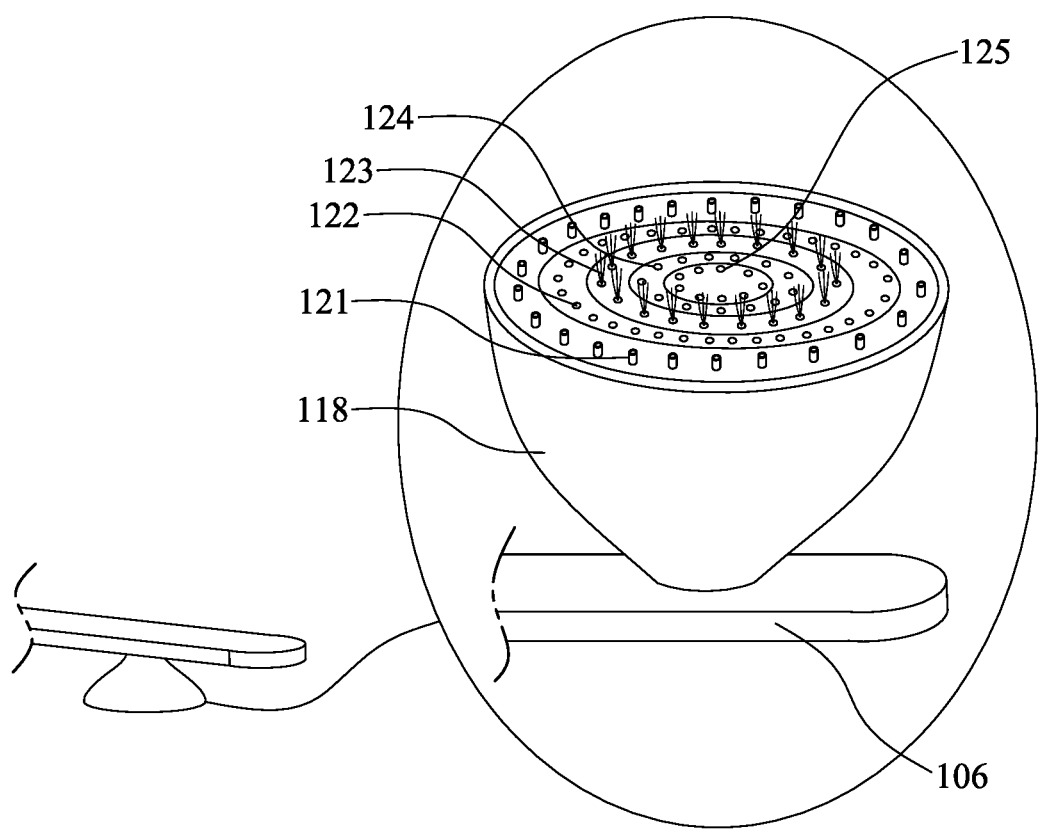
FIG. 3 is an illustration of a primary cleaning unit of the automatic shower system in accordance with the most preferred embodiment of the instant invention.

Referring now to FIG. 3, the primary cleaning unit 118 is adapted to comprise five circular rings including a first circular ring 121 having plurality of uniform nozzles to dispense water, a second circular ring 122 having plurality of uniform nozzles to dispense soap-water, a third circular ring 123 having plurality of brushes for rinsing the head portion 102 H of the user 102, a fourth circular ring 124 having plurality of uniform nozzles for blowing dry air and a fifth circular ring 125 having a plurality of ultraviolet (UV) light sources. The ultraviolet (UV) light irradiated from the fifth circular ring 125 is made to fall onto the head portion 102 H of the user 102. The (UV) light from the plurality of ultraviolet (UV) light emitting sources [LED] acts as a disinfectant or germicidal to the head portion 102 H of the user 102 as well as for the system 100. Each of the brushes mounted in the third circular ring 123 are alternatively adapted to dispense soap-water onto the head portion of the user and further facilitate the rinsing of the head portion 102 H of the user 102.

There is provided a first elevating means adapted to facilitate the controlled and regulated vertical movement of the horizontal frame 106 which in turn facilitates the movement of the primary cleaning unit 118 in an upward and downward direction along the vertical frame 108 with respect to the user 102 standing within the marked region 116. A first elevating means is used to facilitate the controlled and regulated vertical movement of the horizontal frame 106 in an upward and downward direction with the help of chain/thread/belt connected to up and down fixed pulleys working in conjunction with a motor along the vertical frame 108. There is provided a primary guides/tracks on vertical frame 108 to enable the movement of the horizontal frame 106 in the upward and downward direction.

Figure 2:
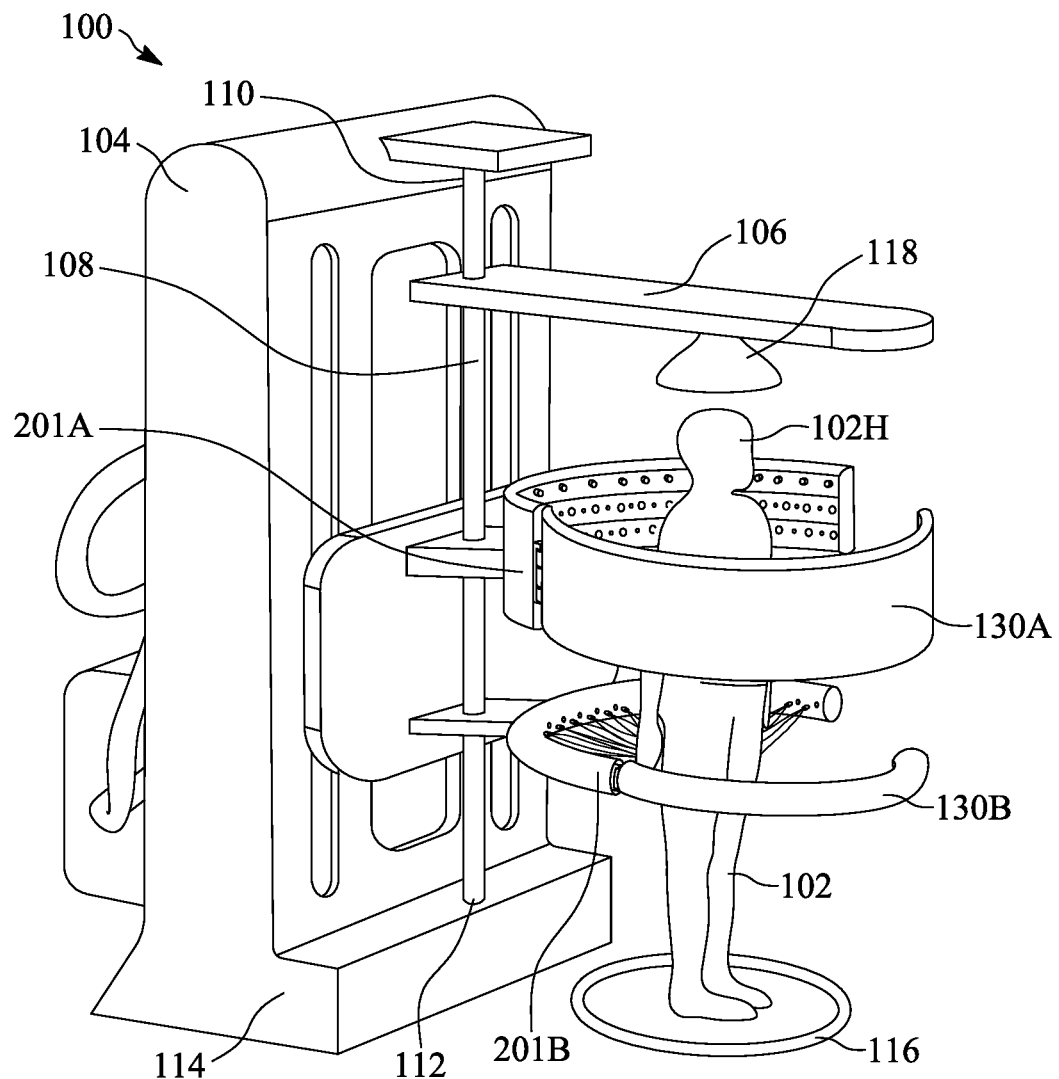
FIG. 2 is an illustration of an automatic system for providing full body shower to a user with shorter height, in accordance with the most preferred embodiment of the instant invention.

In accordance with the most preferred embodiment of the instant invention, there is provided two secondary cleaning units (130 A, 130 B) as shown in the FIG. 1 and FIG. 2. The secondary cleaning units (130 A, 130 B) are preferably in the form of circular rings to cover the full body of the user 102. The rings are either a circular ring, or a semi-circular ring, or an elliptical ring, or a triangular ring, a square ring, a hexagonal ring or a tubular ring. The secondary cleaning units (130 A, 130 B) are configured to be positioned in between the primary cleaning unit 118 and the marked region 116. The secondary cleaning units (130 A, 130 B) are operably coupled to the vertical frame 108 of the supporting unit 104 via ring arms (140 A, 140 B) respectively. The positioning of the secondary cleaning units (130 A, 130 B) is made parallel to the horizontal frame 106 of the supporting unit 104. A second elevating means is used to facilitate the controlled and regulated vertical movement of the secondary cleaning units (130 A, 130 B) in an upward and downward direction with the help of chain/thread/belt connected to up and down fixed pulleys working in conjunction with a motor along the vertical frame 108. There is provided a secondary guides/tracks to enable the movement of the secondary cleaning units (130 A, 130 B) in the upward and downward direction along the vertical frame 108.

Referring now to FIG. 2, the automatic shower system 100 is shown in an alternate position according to user requirement. The primary cleaning unit 118 is moved in the vertically downward direction to provide the enhanced shower experience to a user, more precisely the primary and secondary cleaning units (118, 130 A and 130 B) can be adjusted according to height and width of the user 102. Different user has different height and width and to encompass all shape and size of the users the automatic shower system 100 is made with adjustable height and a variable diameter of primary and secondary cleaning units (118, 130 A and 130 B). The user 102 can also open and close the secondary cleaning unit 130 A and 130 B to enter and exit the shower system 100. Further, each secondary cleaning unit (130 A and 130 B) is equipped with a hinge (201 A, 201 B) respectively to enable the opening and closing of the secondary cleaning units (130 A, 130 B).

Figure 4:
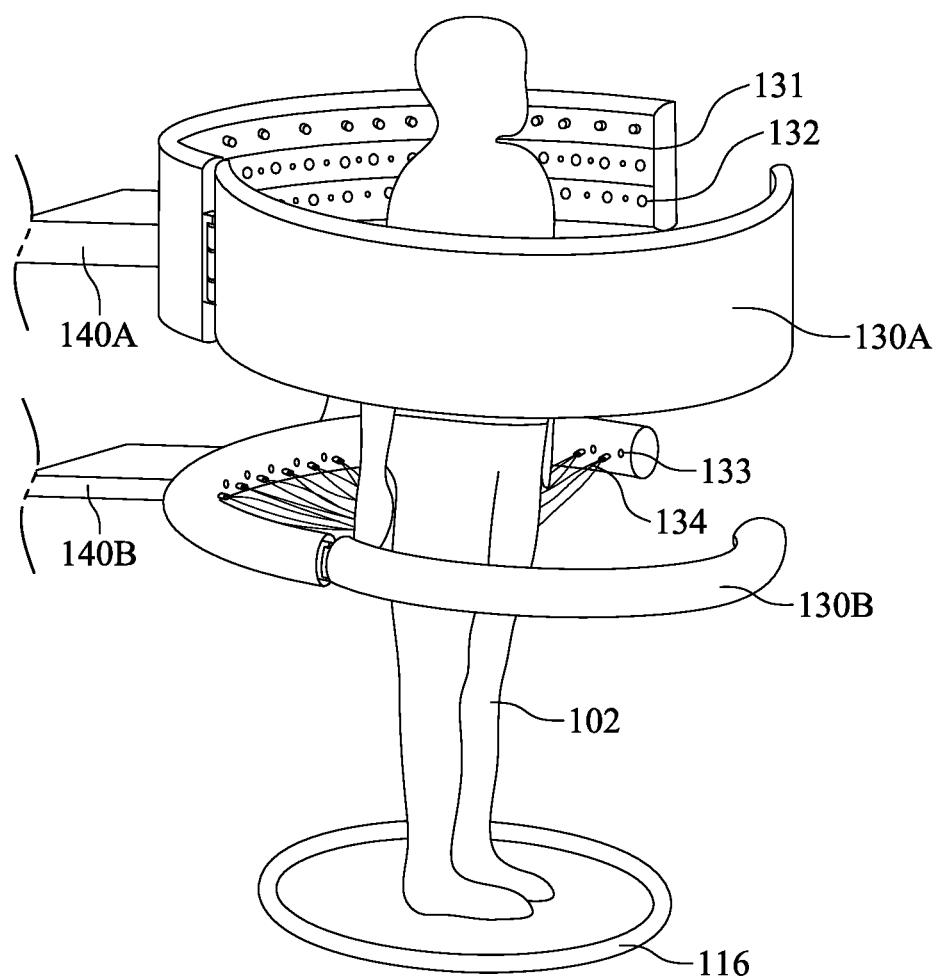
FIG. 4 is an illustration of a secondary cleaning unit of the automatic shower system in accordance with the most preferred embodiment of the instant invention.

Referring now to FIG. 4, the automatic shower system 100 is usually having two secondary cleaning unit 130 A and 130 B, the first secondary cleaning unit 130 A is having plurality of uniform nozzles 131 to dispense the dry air, moisturizer, lotion, soap-water, etc. and a plurality of uniform ultraviolet light sources 132 for disinfecting/germicidal to the user. Further, the second secondary cleaning unit 130 B is situated below the first secondary cleaning unit 130 A to avoid water damping on the first secondary cleaning unit 130 A. The second secondary cleaning unit 130 B has a plurality of uniform nozzles 133 for dispensing water and a plurality of brushes 134 for rinsing the surface of the user 102 body.

Typically, in accordance with the most preferred embodiment of the instant invention, there is provided a waterproof main conduit (Not Shown). The main conduit includes a plurality of secondary conduits that are insulated from each other and made waterproof. The plurality of the secondary conduits and enabling the flow of water, soap-water, moisturizer, ointment, medicament, and serum, etc. to be used for the washing and cleaning of the user. Further the plurality of the secondary conduits enabling the flow of dry air for drying the head portion and the body surface of the user. furthermore, secondary conduit also receiving a plurality of electrical cables including the cables of said first and second elevating means and other power or control cable.

Typically, in accordance with the most preferred embodiment of the instant invention, there is provided an air dryer chamber. The air dryer chamber includes a heating element to heat the air received from an external source and thereby generates dry air. The generated dry air from the air dryer chamber is propelled to the primary and secondary cleaning units through the secondary conduits to facilitate the drying of the head portion and body surface of the user.

Figure 5:
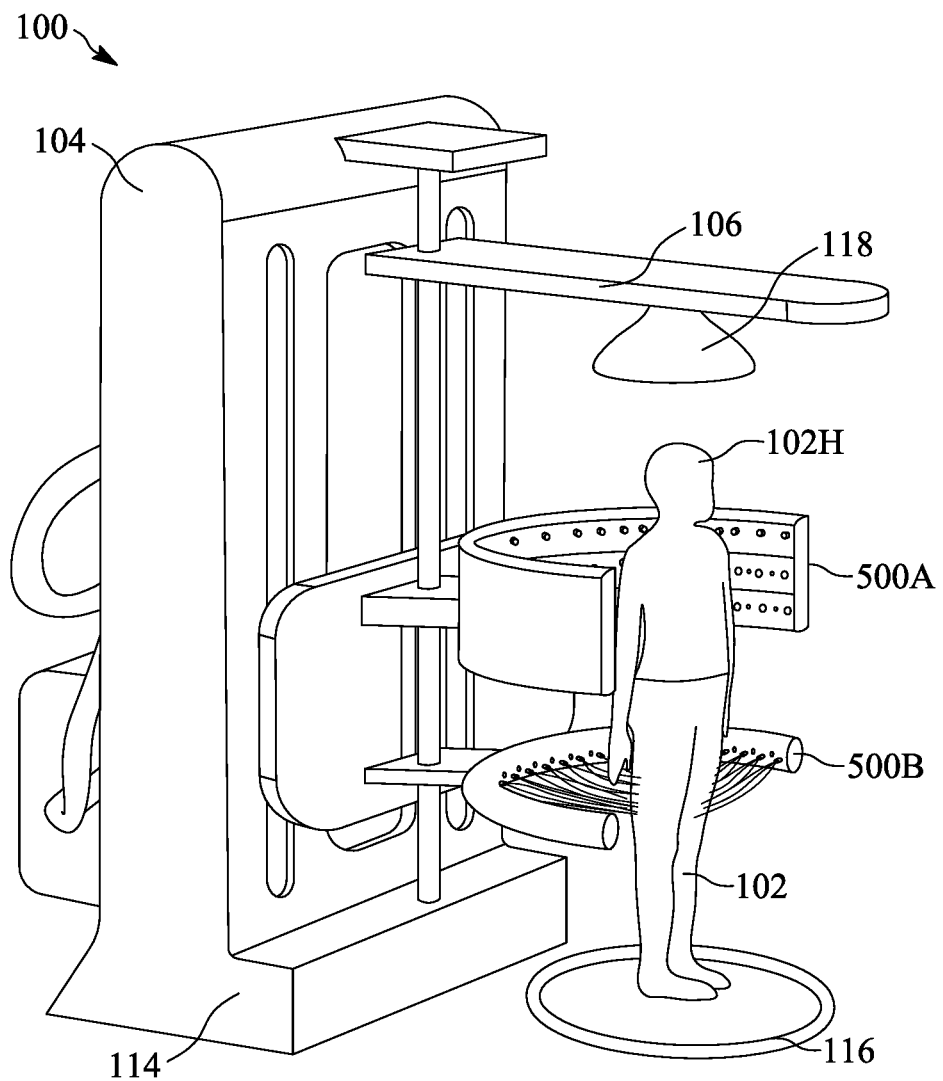
FIG. 5 is an illustration of the automatic shower system with a retractable water pipe for providing full body shower to a user, in accordance with a second alternate embodiment of the instant invention.

Referring now to FIG. 5, the automatic shower system 100 of the FIG. 1 is shown according to a second alternate embodiment, the shower system is unaltered expect the secondary cleaning units of the system are shown in the semicircular form. The semicircular secondary cleaning units 500 A, 500 B have the advantage of reduced cost and hassle free entry and exit of the user. The semicircular secondary cleaning unit is providing full body cleaning and rinsing to the user. Alternatively, the secondary cleaning unit has a bar attached with a hinge at the open ends of the semicircular secondary cleaning unit and having a plurality of brushes to clean the user body. Further, the user can open and close the secondary cleaning unit by clutching the bar from one end.

Figure 6:
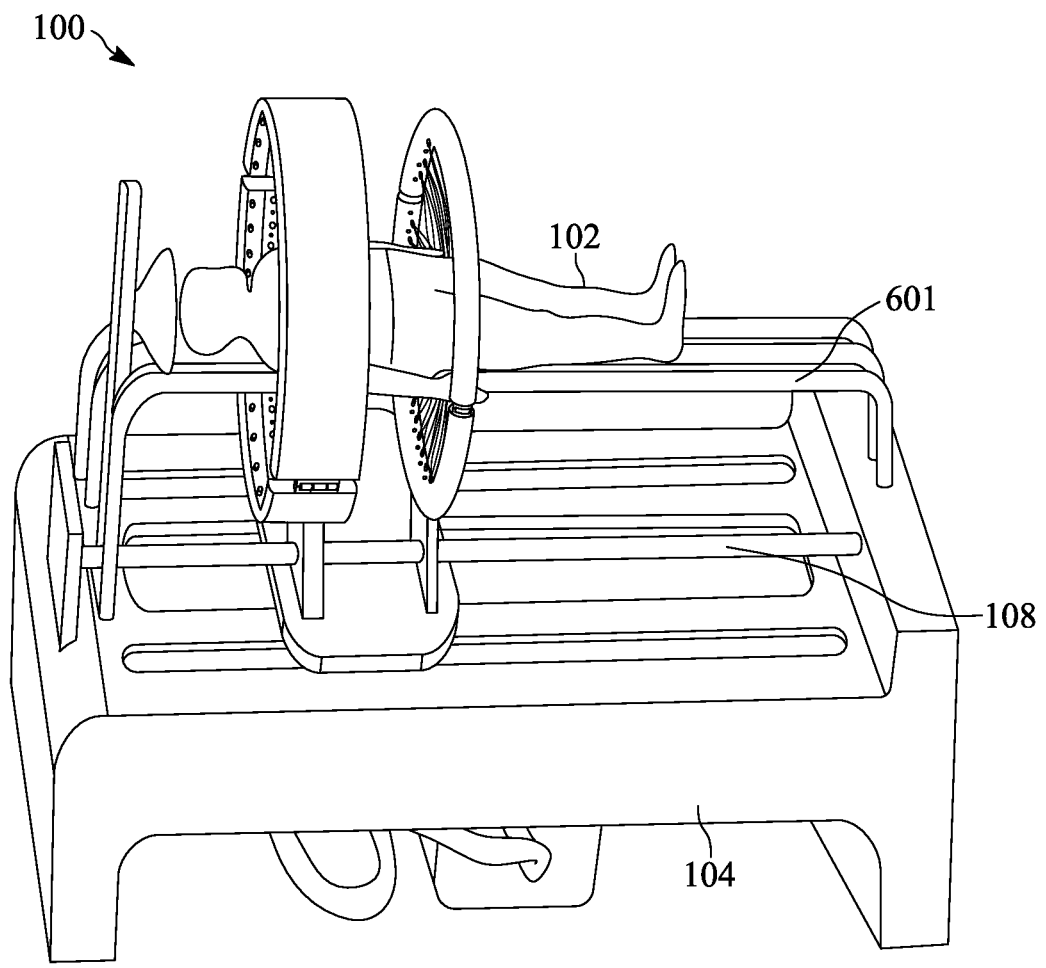
FIG. 6 is an illustration of the automatic shower system for providing full body shower to a user in a horizontal orientation, in accordance with the fourth alternate embodiment of the instant invention.

Referring now to FIG. 6, the automatic shower system 100 as shown in a third alternate embodiment is shown in a horizontal orientation. Further, in the horizontal orientation, the automatic shower operations are the same as vertical orientation except it requires additional accessory of horizontal beams 601 that are extending from the lower end portion of the supporting unit 104 to the upper end of the supporting unit 104. The length of the horizontal beams is made sufficient enough to accommodate the user body. To use the automatic shower system in horizontal orientation the user lays on horizontal beams 601 and the secondary cleaning units are moves from left to right or right to left to clean the user 102 body completely.

According to various embodiments of the instant invention the automatic shower system may have more than one secondary cleaning unit detachably attached to the ring arms as per the requirement for separately dispensing the water, soap-water, moisturizer, UV light, dry air, etc. Further, the scope of the instant invention is including but not limited to the shape of the rings, the rings are either a circular ring, or a semi-circular ring, or an elliptical ring, or a triangular ring, a square ring, a hexagonal ring or a tubular ring. Further, the various dispensing units in the secondary and the primary cleaning units can be mounted in any order (up and down) as per the user requirement more precisely the uniform nozzles dispensing water, soap-water, moisturizer etc. and the brushes and UV lights can be mounted on the aforesaid cleaning unit in any manner. Additionally, the automatic shower system may have a single secondary cleaning unit encompassing all the uniform dispensing nozzles, UV light sources and Brushes.

Further each of the ultraviolet (UV) light sources used in the automatic shower system 100 is preferably a light emitting diode (LED). The ultraviolet (UV) light from the light emitting diode [LED] is made to fall onto the body surface of a user. The (UV) light from the light emitting diode [LED] acts as a disinfectant to the body region surface of the user.

According to various embodiments of the instant invention there is provided a display unit (Not Shown). The display unit is adapted to display a plurality of attributes of the functional elements of the automatic shower system. Further, the display unit is used to enable the user to control a plurality of functional elements in the system. Wherein the at least one attribute of the automatic shower system is either the temperature of the water used in the shower, or the flow of water, or the flow of dry air, or the positioning of each of the first and second elevating means, or the quality and quantity of soap-water, or the characteristic of light from each of the ultraviolet (UV) light sources, or dispensing of the moisturizer, serum medicament on to the user.

According to various embodiments of the instant invention there is provided a plurality of sensor for detecting the characteristics of various aforesaid attributes and providing input to the main control unit. Further, the plurality of sensors including a sensor for detecting the presence and to identify the position of the user within the marked region is also available in the automatic shower system. The automatic shower system is automatically switched OFF when there is no presence of the user within the marked region and automatically switched ON when there is a presence of the user within the marked region. The sensor is configured to transmit the communication signal to the microprocessor in the main control unit regarding the presence and non-presence of the user within the marked region. The microprocessor, after processing the information is adapted to switch OFF the automatic shower system if there is no user within the marked region and switch ON the automatic shower system when there is a presence of the user within the marked region. The main control unit is further adapted to control the functioning of a plurality of functional elements in the automatic shower system including the functioning of the primary and secondary cleaning units, the first and second elevating means, the ultra-violet (UV) light sources, the display unit, the sensor, and the air dryer chamber.

Further according to various embodiments of the instant invention there is provided an auxiliary unit adapted to position the patients, old age people and persons with limited motional ability within the marked region with ease.

To use the shower system the user enters into the system or shower cubicle and provides specific inputs through the display unit by submitting specific requirements and values of the attributes. Upon receipt of all the specific attributes, the sensor detects the presence and identifies the position of the user within the marked region and the shower cycle is initiated. After the initiation of the shower cycle, the primary cleaning unit and the secondary cleaning units are automatically moves upward or downward direction as per the user requirement in the case of horizontal orientation of the shower system the primary cleaning unit and the secondary cleaning unit move in left and right direction with the help of primary and secondary elevating means to adjust according to user's shape and size. Further based on the predetermined inputs the uniform nozzles of primary and secondary cleaning units dispenses the water, soap-water, medicament, serum, and dry air etc. further to this the brushes in the primary and secondary cleaning units are adapted to rinse the user body followed by the dry air blower to dry the surface of the user body and UV light for germicidal or disinfecting purpose. Once the shower cycle completes the automatic shower system alerts the user by notifying through a buzzer, voice-over etc. then the user opens the hinged secondary unit and exits the system. The sensor detects the absence of the user and initiates the controller to disinfect the machine by UV lights and then turn itself OFF. The system facilitates the user to store the setting of the parameters in a user profile to reuse the shower system based on the predefined settings.

According to various embodiments of the instant invention the material of each of the brushes or bristles is either soft fabric, polymeric or a fiber or a microfiber. Each of the brushes in the secondary cleaning unit is adapted to suit various sensitive skin types of the users of the automatic system.

According to various embodiments of the instant invention the uniform dispensing nozzles and the plurality of brushes may have rotational ability to provide enhanced cleaning and rinsing of the user body.

The display unit interacts with the system through the user interface provided therein. The various module options provided therein in the user interface include, among others, option for choosing head shower/bath or without head shower/bath, soap quantity, brush rinse cycle, drying intensity, brush strokes intensity, mild, gentle or intensive, water temperature, exact height of user or this can be automatically calculated based on sensor fixed on vertical stand, once selected. Furthermore, as an essential requirement for the usage of the system, the user should wear swimming eye protection glasses and ear cap to protect from soap dispensing on eyes and ears, and the user should stand into the marked region, shower cycle will start accordingly. The selection made by the user through the user interface is automatically saved in the system as a user profile which can be selected by the user in the future without any need to enter all the settings.

Further in between the shower cycle the buzzer makes a sound or recorded audio voice asks to lift the hands to clean up under arms, but this is an optional feature, same for lower abdomen cleaning also. If the user tries to leave abruptly during the shower cycle by asserting some pressure on the secondary cleaning unit, then the shower cycle will be stopped or paused. The cleaning unit waits until the user is back into the marked zone. Once the user is into the marked zone, the shower cycle is initiated again.

Figure 7:
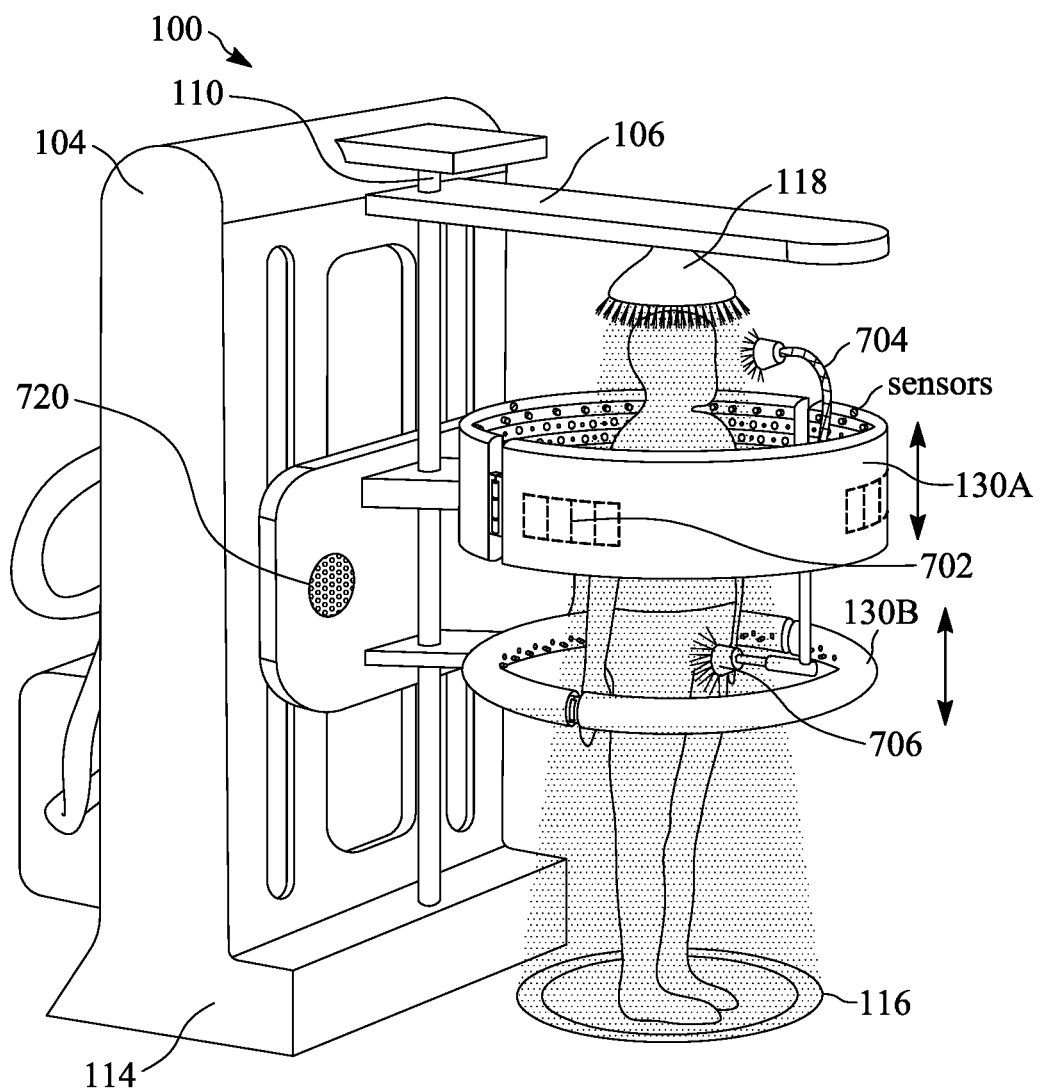
FIG. 7 is an illustration of the automatic shower system for providing full body shower to a user, in accordance with a second alternate embodiment of the instant invention.

Referring now to FIG. 7, a user is standing within the marked region 116 to take full body shower/bath/cleaning using the automatic shower system. The secondary cleaning units (130 A, 130 B) are configured to be positioned in between the primary cleaning unit 118 and the marked region 116. The secondary cleaning units (130 A, 130 B) are provided with provisions for multiple compartments or chamber 702 to add soap, moisturizer fragrance etc. Each of the chamber is provided with a button for the user to select the different brands for each type of soap, moisturizer fragrance. The secondary cleaning units 130A is provided with a retractable water pipe or brush 704. The user can retract the water pipe/brush 704 to apply water over the face area to ensure cleaning of face area properly. Similarly, the secondary cleaning unit 130B is provided with a retractable water pipe cum brush 706. The retractable water pipe cum brush 706 is located under or top of the secondary cleaning unit 130B. The retractable water pipe cum brush 706 is used by the user to clean private area. The water pipe cum brush 706 can be retracted by the user to reach the private area and manual cleaning of private area. In some embodiment, the water supply is provided in both the secondary cleaning units 130A and 130B, to allow user to use retractable water pipe cum brush 704 and 706.

In an embodiment, a speaker 720 is provided in the automatic shower system 100 to make announcements or to notify the user taking shower. The speaker 720 is waterproof so as to prevent it from physical damage.

In other embodiment, when a user stands inside the marked region 116, the sensors present in the automatic shower system measures the length, weight and height of the user. The automatic shower system 100 calculates the BMI (Body Mass Index) of the user and announces through the waterproof speakers 720.

The sensors of the automatic shower system notifies the processing unit that determines the optimal height of the primary cleaning unit 118 and accordingly sends instructions to adjust the height of the primary cleaning unit 118.

Figure 8:
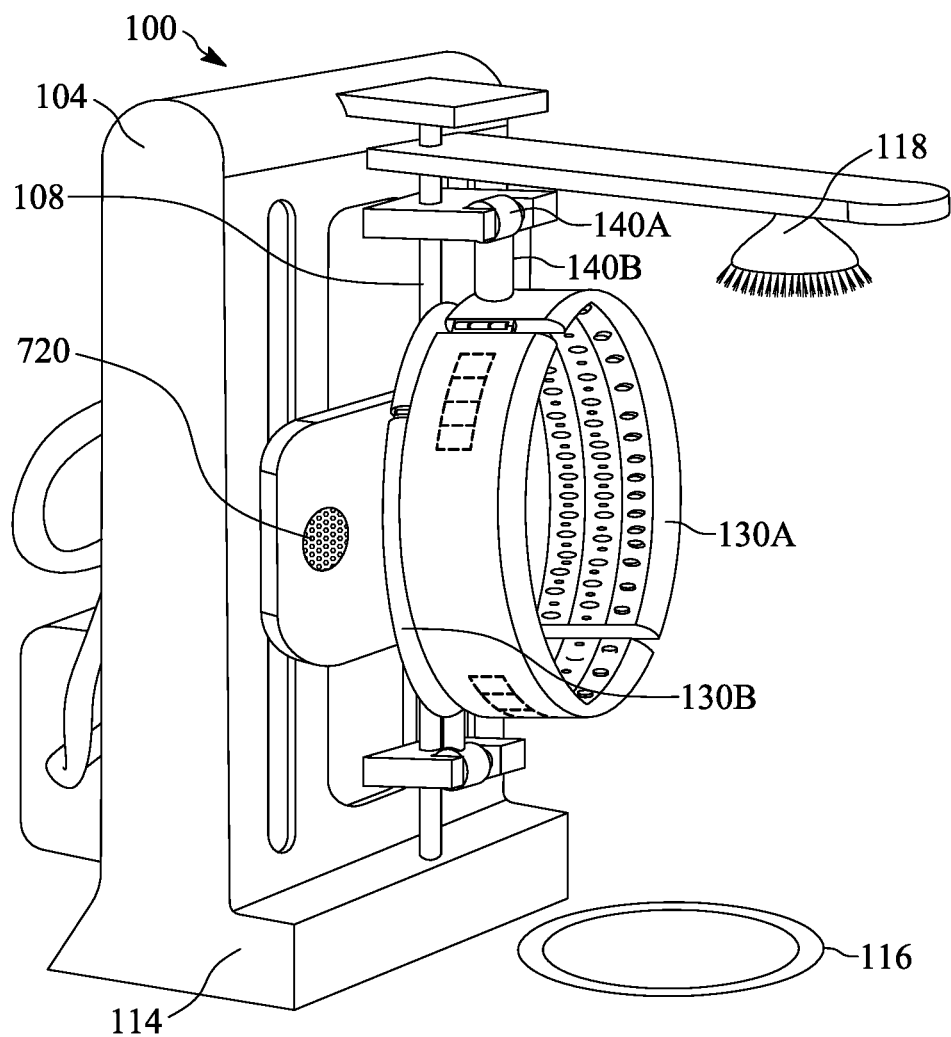
FIG. 8 is an illustration of the automatic shower system when not in use, in accordance with a second alternate embodiment of the instant invention.

Referring now to FIG. 8, it illustrates the automatic shower system when it is not in use. The secondary cleaning unit 130A and 130B are connected to ring arm 140A and 140B through pivot joints. When the automatic shower system 100 is not in use, the secondary cleaning unit 130A and 130 B retracts inside vertically and positioning of secondary cleaning unit becomes parallel to the vertical frame 108. When a user wishes to take full body shower he stands within the marked region 116 and the system gets activated. The secondary cleaning unit 130A and 130 B retracts perpendicularly and positioned themselves parallel to the horizontal frame. In some embodiments, provision for non-automatic or manual shower is provided. The secondary cleaning units 130A and 130B remains in folded positions so as to allow the user who wants to take non-automatic or manual shower, can do when it is in folded position.

Figure 9:
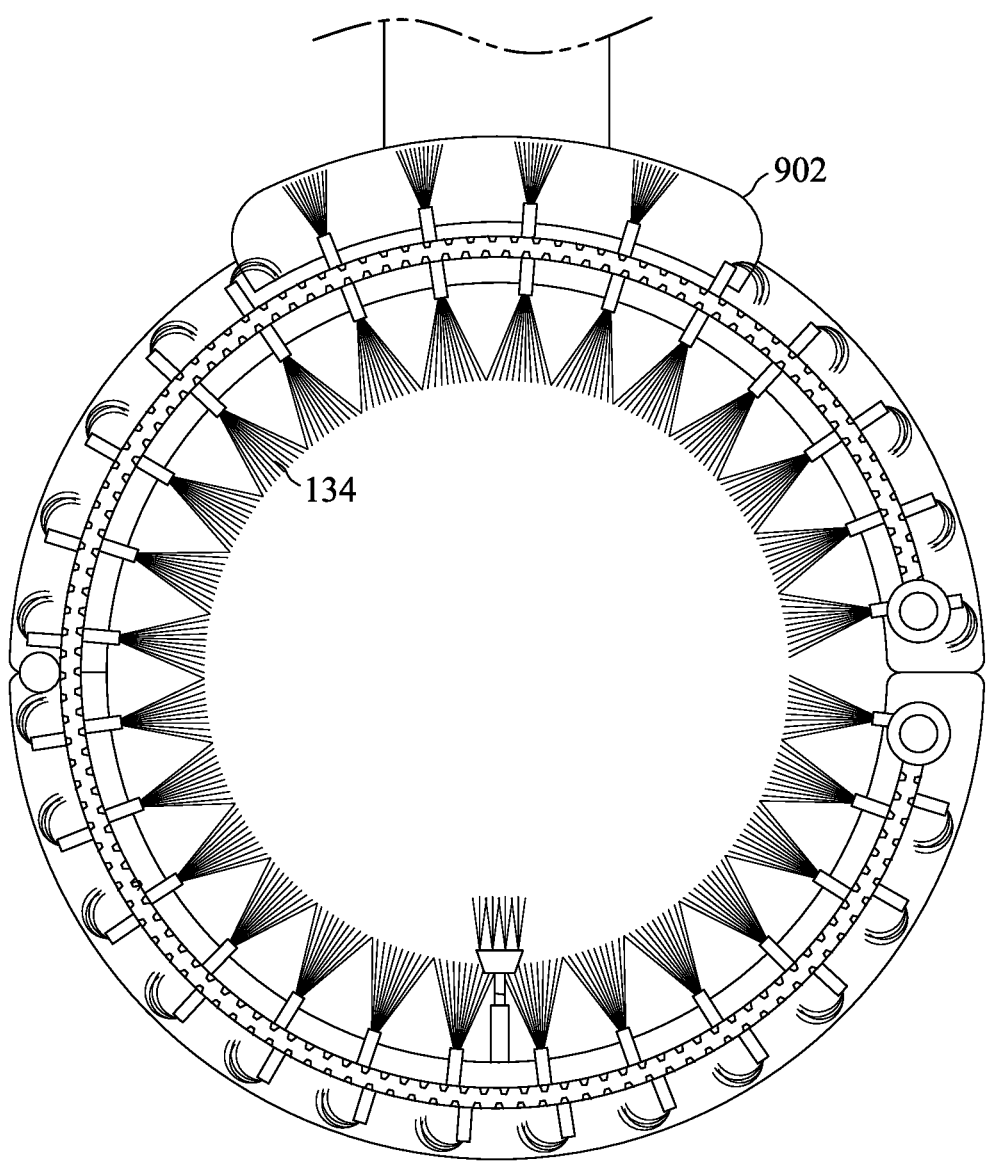
FIG. 9 is an illustration of the automatic shower system with brush cleaning chamber in the ring, in accordance with an embodiment of the instant invention.
Figure 10:
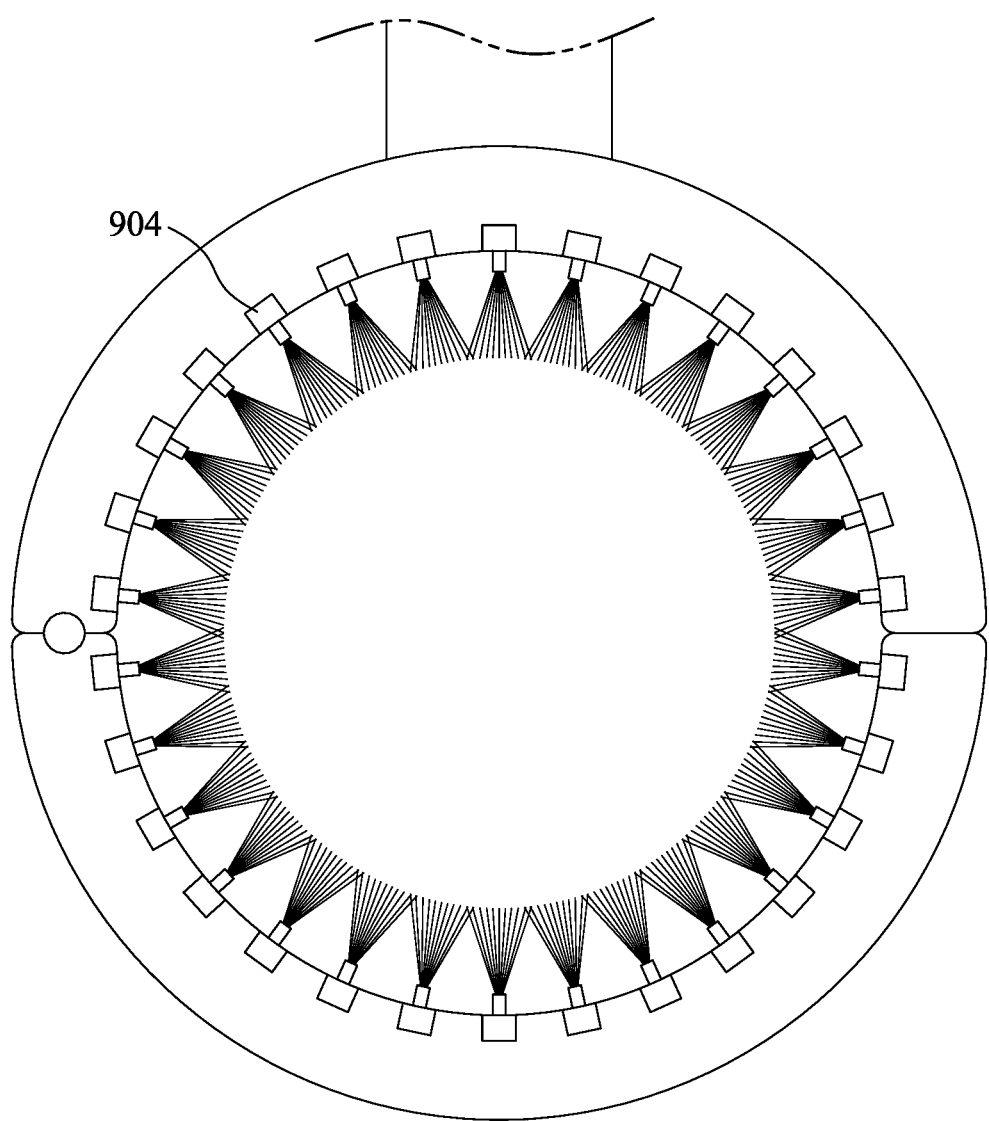
FIG. 10 is an illustration of the automatic shower system showing brush with a dedicated motor, in accordance with an embodiment of the instant invention.

Referring now to FIGS. 9 to 10, the provision for cleaning brush is illustrated. The secondary cleaning unit 130A and 130 B has a plurality of uniform nozzles for dispensing water and a plurality of brushes 134 for rinsing the surface of the user body. The secondary unit 130A and 130 B are in form of circular or semi-circular rings. The rings can expand and decrease to meet different sizes of human bodies. As shown in FIG. 9, the ring contains a brush cleaning chamber 902 positioned on the outer side of the ring. The chamber is either at a fixed location wherein the brush is pulled backward so as to expose each of the brush in the brush cleaning chamber 902. In other embodiment, the brush cleaning chamber 902 is moveable relative to the ring. The brush 134 are cleaned in the brush cleaning chamber 902 and the motor 904 retracts the brush back to the original position on the ring. In other embodiment, the motor 904 pulls back the conveyor belt type brush in the brush cleaning chamber 902 and replace the brush ribbon present in an external box. In an embodiment, each of the brush 134 is attached to separate motor 904. The user can select the brush 134 which he wants to operate on specific areas. The rest of the brush 134 can stay off.

FIG. 10 is an illustration of the automatic shower system showing a brush with dedicated motor, in accordance with an embodiment of the instant invention. In the brush cleaning chamber 902, the brush 134 is retracted through a motor 904, as shown in FIG. 10. Each of the brush 134 is provided with a dedicated motor 904. The user can control which area he wants to use or not to use as per the need of the user. The individual motor 904 projects the brush outwards which only operate on area where the user wants or not to project the brush also, while the remaining brushes can stay off.

Figure 11:
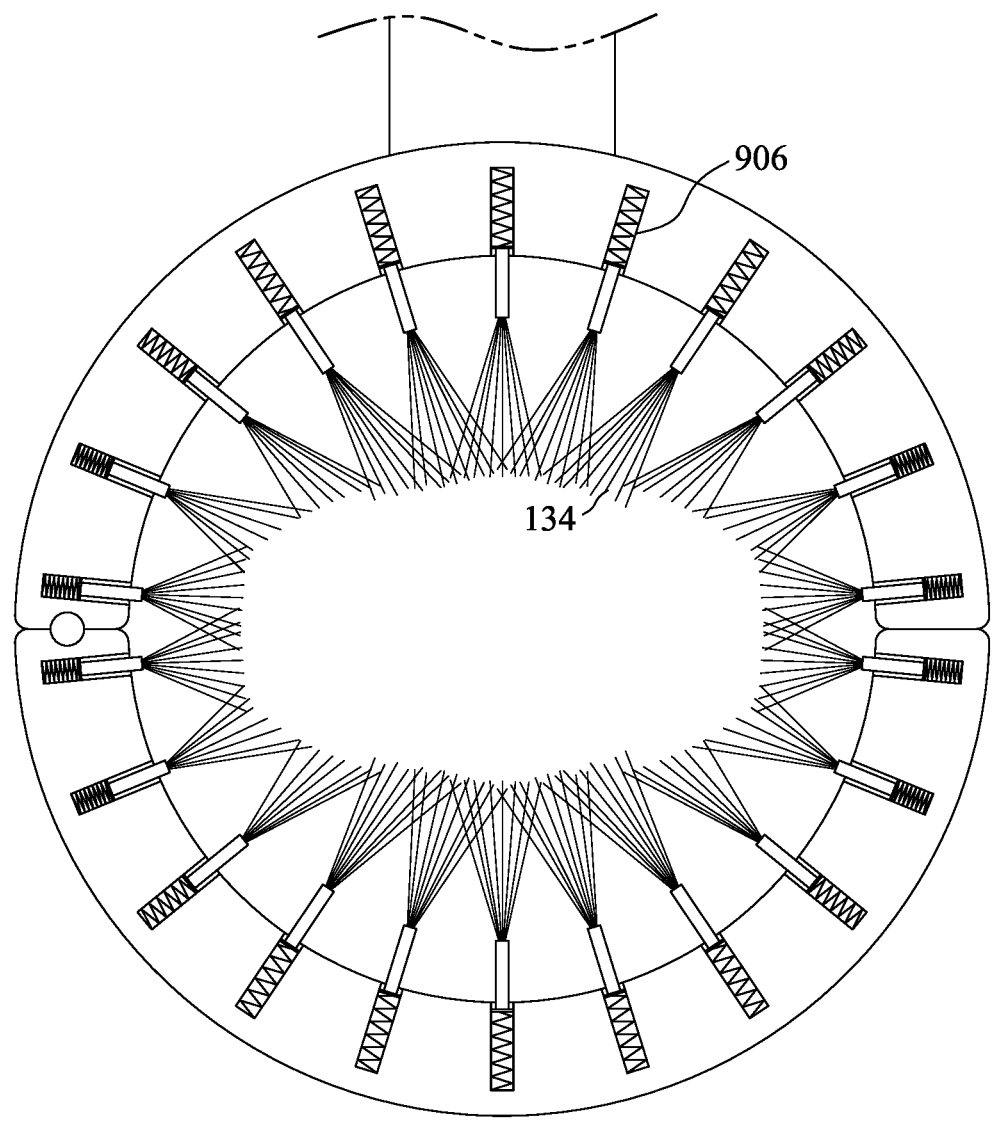
FIG. 11 is an illustration of the automatic shower system with brushes loaded with spring loaded arms or rods to touch the user's body with enough contact especially for different sizes and shapes of users bodies, in accordance with an embodiment of the instant invention.

Referring now to FIG. 11, the auto length adjusting brush is illustrated. The brush 134 are present on the spring loaded arm 906. In other embodiment, the spring loaded arm 906 is activated in automatic way to retract the brush 134 in order to clean the user body. The auto shower brush 134 are at the end of the spring loaded arm 906 or multiple rods and retracted automatically to touch the whole body of the user with enough contact equally to wash. The automatic brush fits the contour of whole user's body with precise contact to wash effectively of the while body of the user. The spring loaded arm 906 ensures that even to irregular body shapes, enough pressure is applied for cleansing purpose. The spring loaded arm 906 can be controlled through application, a processing unit and a circuit board to apply pressure precisely in controlled manner. The secondary cleaning unit 130 B is equipped with brush loaded at the end of spring loaded road. These brush can release and contract according to the contour of the body to brush the skin precisely.

Figure 12:
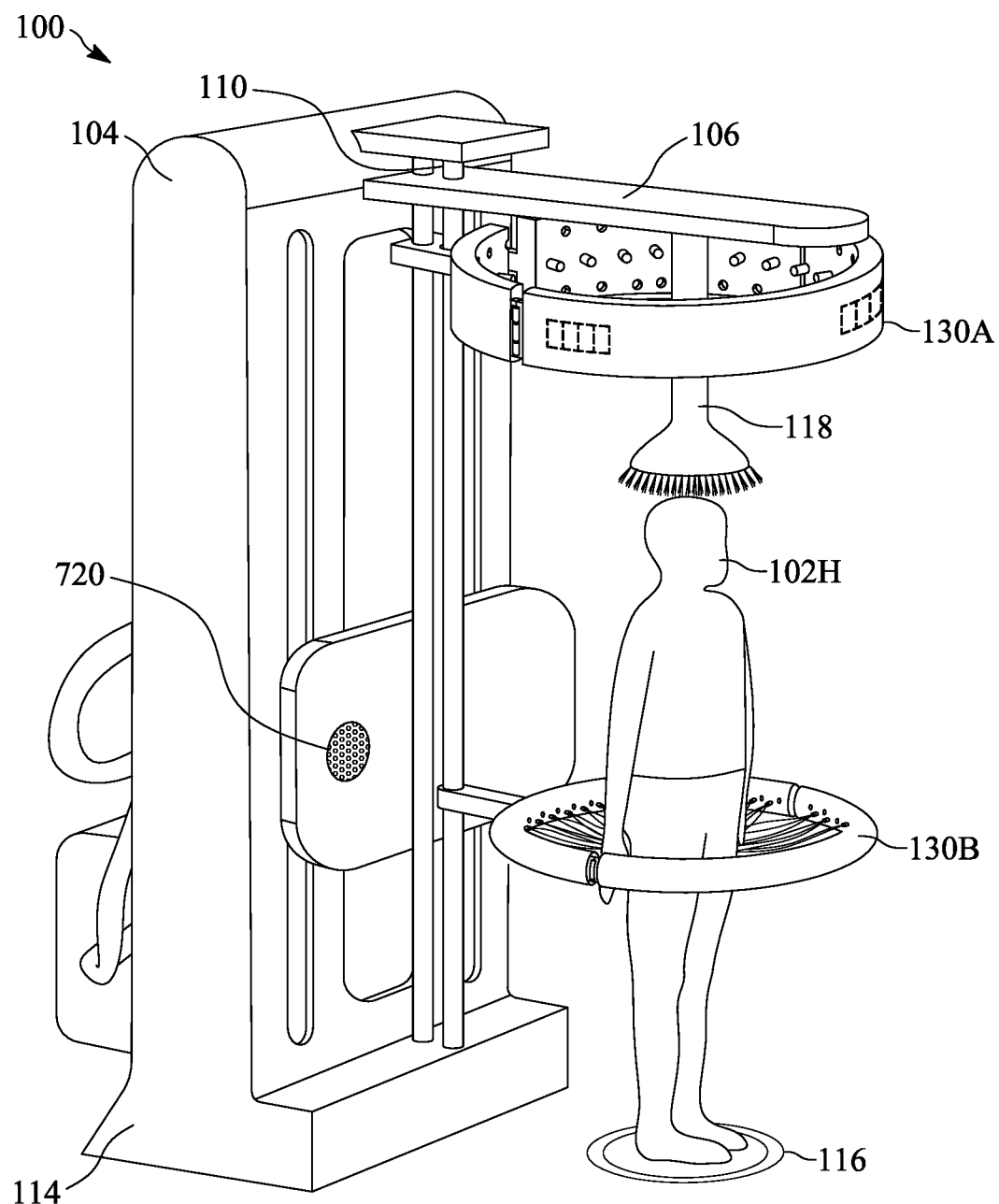
FIG. 12 is an illustration of the automatic shower system with one of the secondary cleaning unit in hold position and waiting over there, in accordance with an embodiment of the instant invention.

Referring now to FIG. 12, the automatic shower system with a user standing inside the marking with brush contacting the user body is shown. Based on the duration and time lapsed, the secondary cleaning unit 130A and 130B can be controlled to perform one function at a time. For instance, in FIG. 12, the secondary cleaning unit 130B is operating to perform the dryer function. At any time, one of the secondary cleaning unit can be operational or both the secondary cleaning units are operational. The optional functioning is provided so as to prevent the user from feeling congested or suffocated due to multiple functions at a time.

In another embodiment, the functioning of secondary cleaning unit 130A and 130B can be provided in a single ring, which eliminates the need for providing two separate rings.

Figure 13:
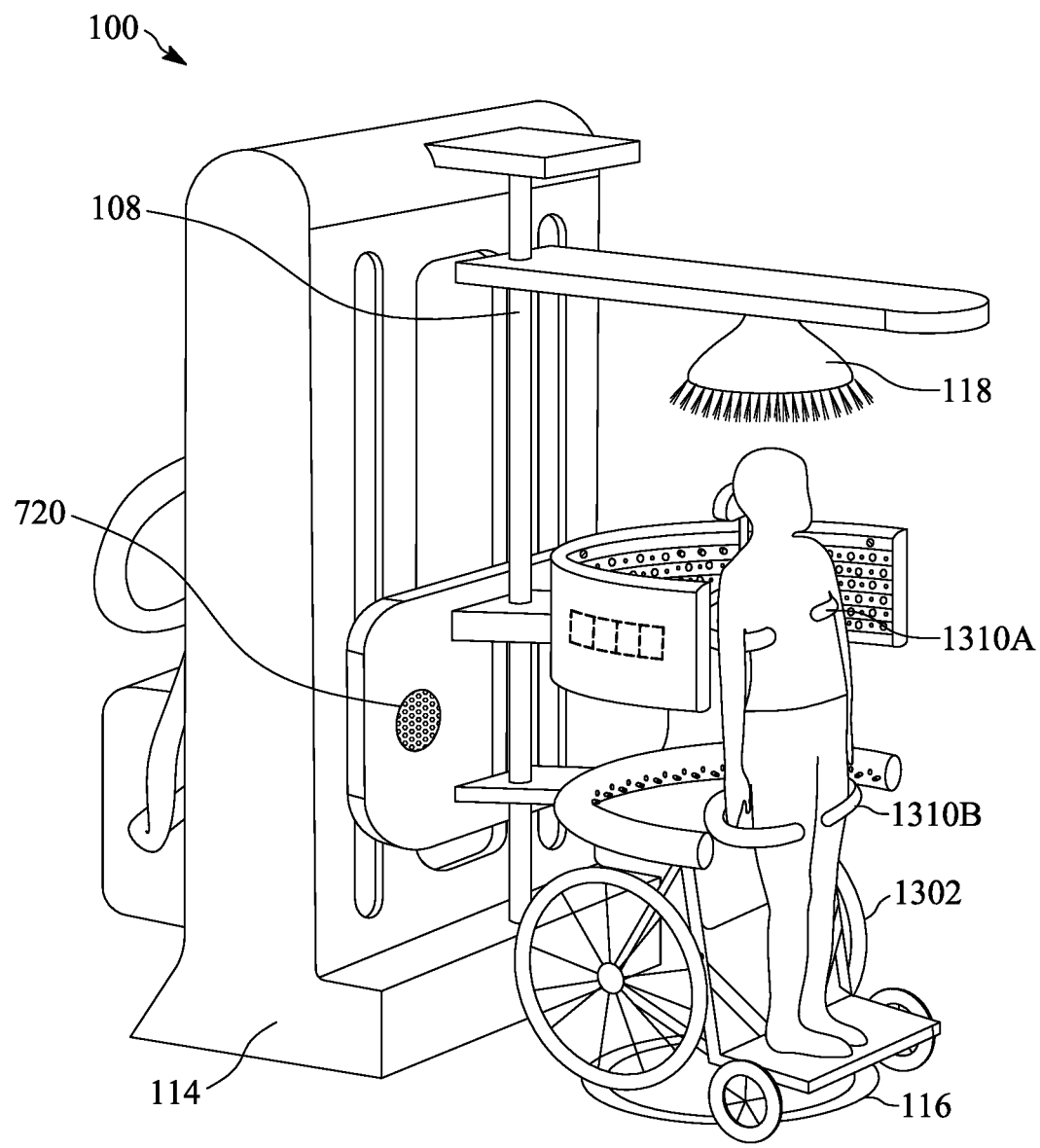
FIG. 13 is an illustration of the automatic shower system with provision of people using wheelchair, in accordance with an embodiment of the instant invention.
Figure 14:
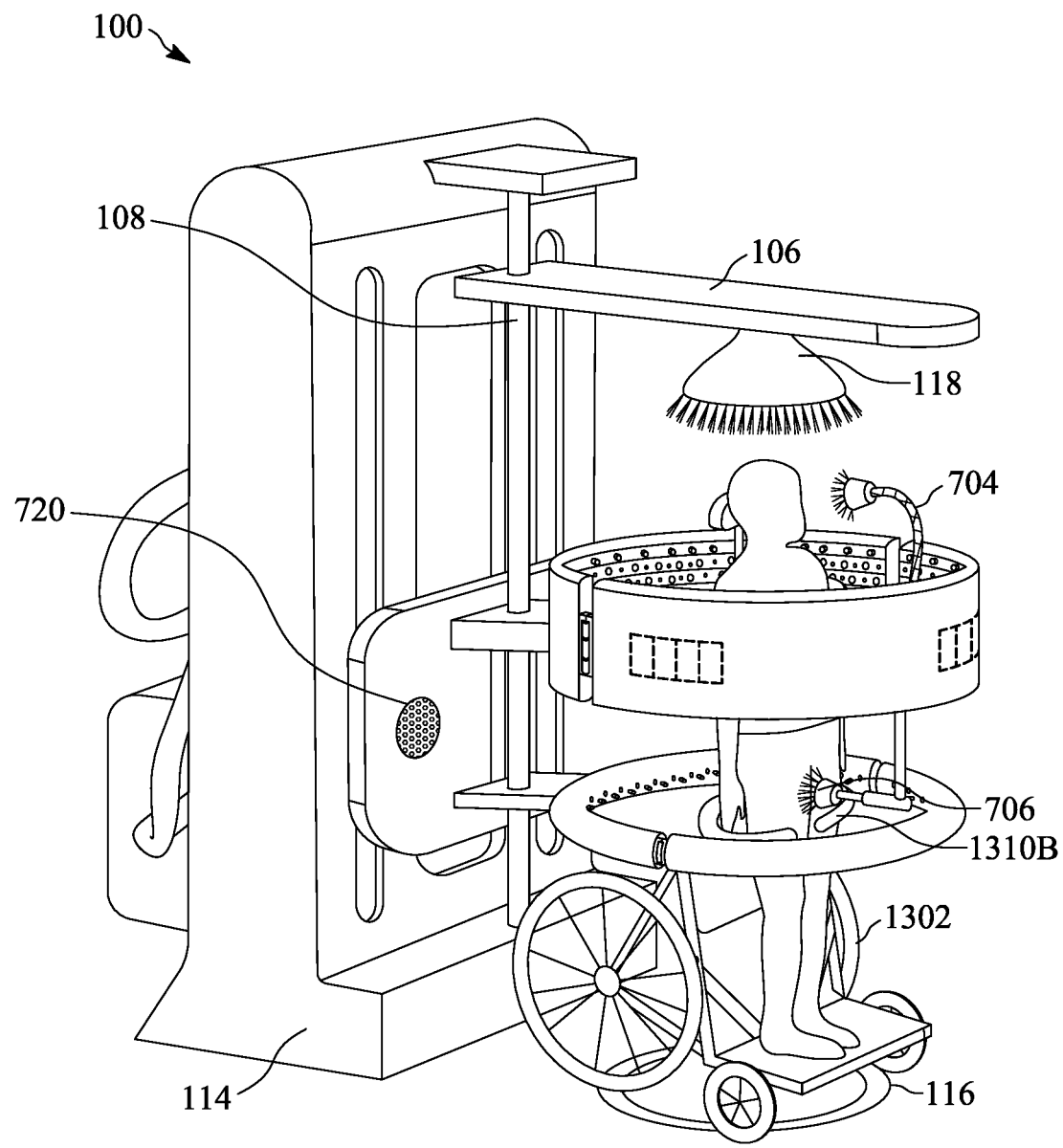
FIG. 14 is an illustration of the automatic shower system with a disabled user standing using a standup feature with rings closed, in accordance with an embodiment of the instant invention.

Referring now to FIG. 13 and FIG. 14, provision for a user who uses wheelchair is provided in the automatic body shower system. The wheelchair 1302 can be pushed directly inside the automatic shower cabinet for shower. The automatic shower system 100 has a space to lock the wheelchair 1302. The wheel chair is having option to slowly lift the person straight standing position with a pair of supporting rings 1310A and 1310B. The supporting ring 1310 B provide support to the lower waist area of the user and the supporting ring 1310A provide support to upper portion of the user wherein the supporting ring 1310A is positioned below the shoulders of the user. The supporting ring 1310A and 1310B are oriented parallel to the horizontal axis. When a user with wheelchair 1302 enters the marking area, the automatic shower system 100 gets activated. The user can place the wheelchair 1302 in the space provided in the automatic shower system 100 facing the front side of the system 100. The supporting ring 1310A encircles the user around the chest area just below the shoulders. The user can rest his shoulders on the supporting ring 1310A, which then moves upwards vertically to lift the user in standing position. The supporting ring 1310B encircles around the lower waist area to provide support to the lower body. The user in upright position supported with the supporting rings 1310A and 1310B is able to take shower/bath in the automatic shower system 100. The secondary cleaning unit 130A and 130B along with the primary cleaning unit 118 get activated and provide bathing features to the user. FIG. 14 shows a user with wheelchair 1302 taking shower in the automatic shower system 100. The user is standing in upright position with the help of supporting rings 1310A and 1310B. The secondary cleaning unit 130A and 130B with retractable shower and brushes clean the body and private part thoroughly.

Figure 15:
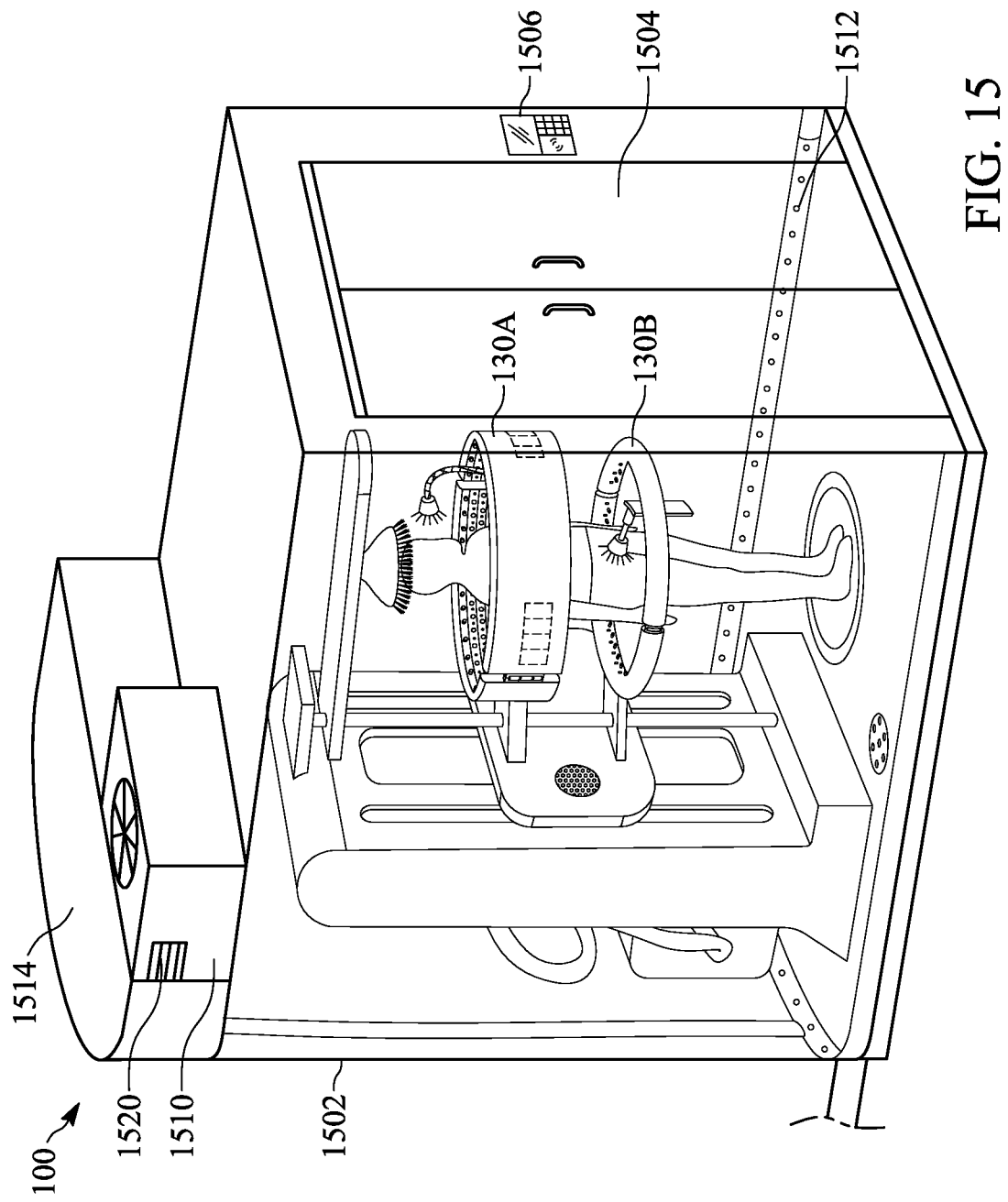
FIG. 15 is an illustration of the automatic shower system enclosed in a cabinet, in accordance with an embodiment of the instant invention.
Figure 16:
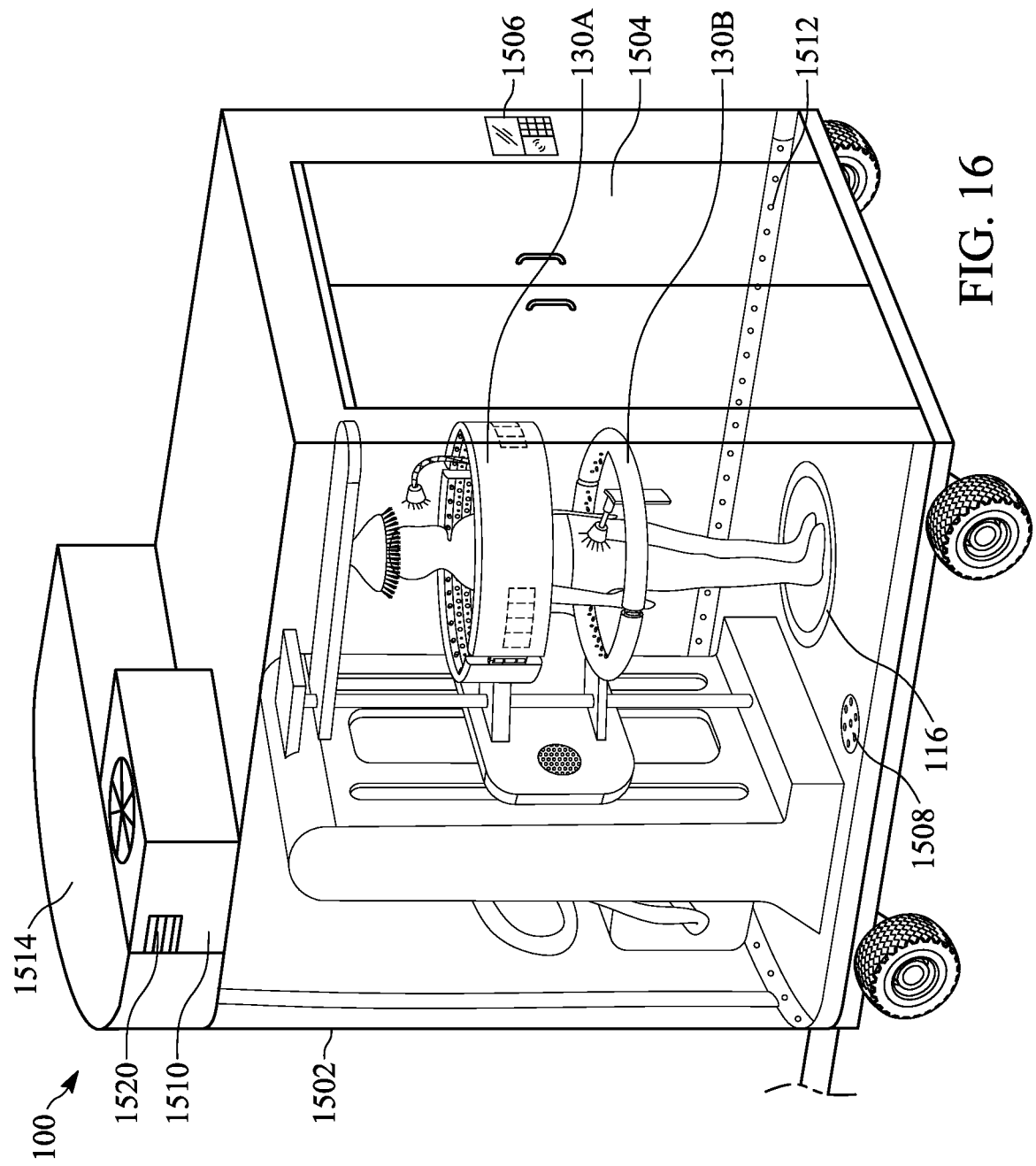
FIG. 16 is an illustration of the automatic shower system enclosed in a movable cabinet, in accordance with an embodiment of the instant invention.

Referring now to FIGS. 15 and 16, the automatic shower system within a cabinet 1502 is illustrated. The automatic shower system 100 is provided with a cabinet 1502 to stop water spill over outside. A door is 1504 provided in the cabinet 1502 for entry in the automatic shower system. In some embodiment, a button or a user interface 1506 is provided in the cabinet to open the door. When the user presses button on the cabinet, the door 1504 opens automatically and simultaneously secondary cleaning unit 130A and 130B open so that user can enter into the shower. After the user enters within the marked region 116, the door 1504 closes and automatic shower system 100 starts operating. The used water from the automatic shower system 100 is drained through water drain 1508. The cabinet 1502 has an air ventilation unit 1520 to avoid moisture or condensation or fog buildup. The cabinet 1502 is also provided with an air conditioning unit 1510 to maintain proper temperature inside the cabinet. The cabinet is equipped with a blower 1512 to blow warm air from the floor of cabinet to dry the cabinet after use.

In some embodiment, a water storage tank 1514 is provided on top of the automatic shower system 100. The water in the storage tank 1514 is useful in case of power failure so that water can be released to complete bath or shower.

In some embodiment, the cabinet 1502 are equipped with wheels to impart mobility to the automatic shower system 100.

Figure 17:
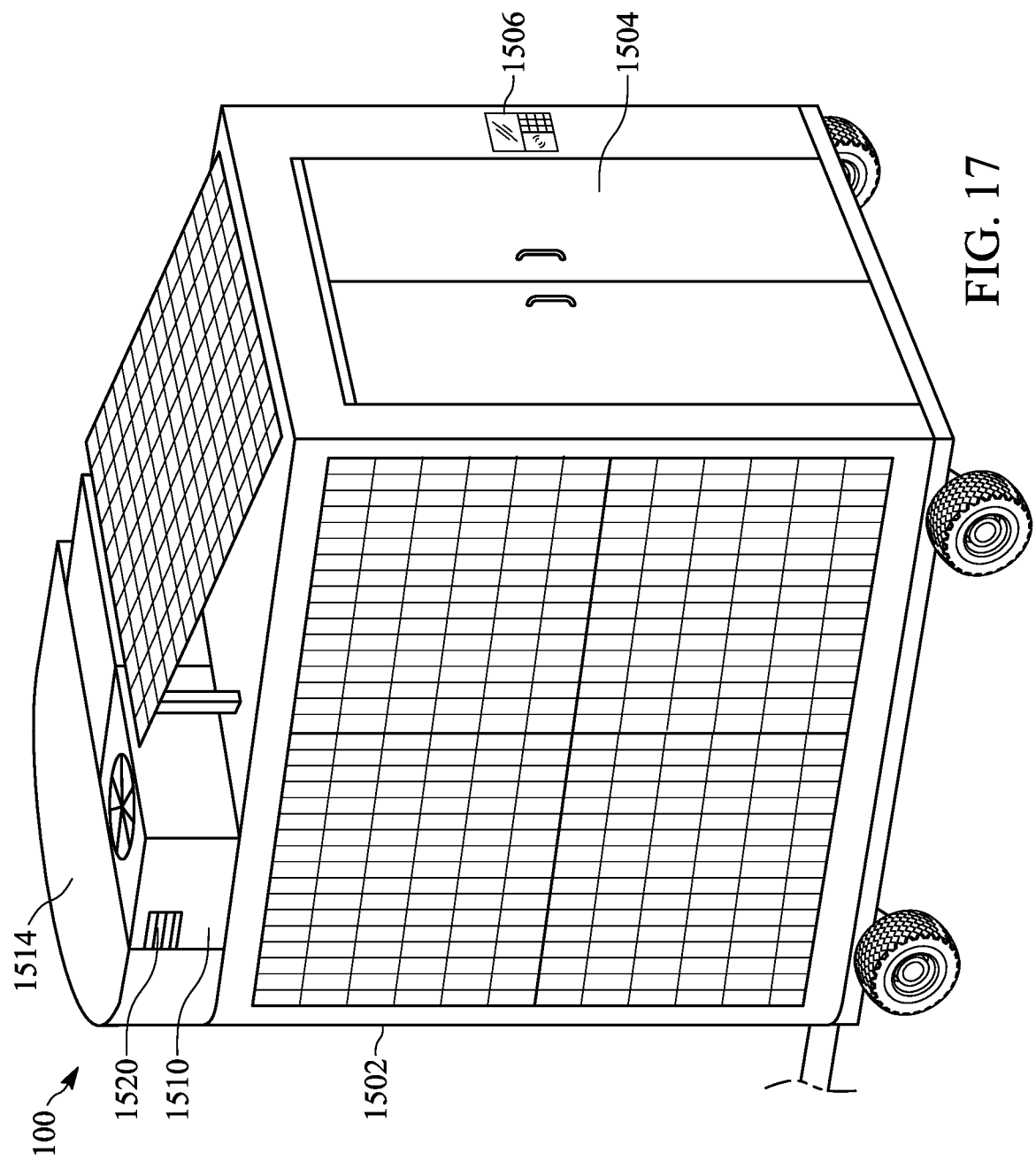
FIG. 17 is an illustration of the automatic shower system for outdoor community shower having a water storage tank and a renewable power source, in accordance with an embodiment of the instant invention.

Referring now to FIG. 17, an automatic shower system equipped to harness power from renewable energy source is provided. The cabinet 1502 enclosed automatic shower system 100 can be used for community shower. The top and side wall of the cabinet 1502 are fitted with solar panels to harness the electrical energy. The harnessed electrical energy is stored on battery that acts as a power back up option which can be used especially in remote locations where power access is not available.

Technical Advantages and Economic Significance of the Invention

The instant invention provides an energy efficient, time saving and water saving automatic system that facilitates full body shower to a user. The automatic system as disclosed in the instant invention when used as a shower system is configured to provide 360° round the body cleaning to a user. The system as disclosed in the instant invention facilitates full body shower to all users including users with limited or differential mobility. In addition, the system as disclosed in the instant invention includes a cleaning and drying facility comprising a plurality of automatic dispensers. The system as disclosed in the instant invention can be used as both vertical as well as horizontal shower system and is further configured to enhance the personal hygiene of the user. As disclosed in the instant invention, the system is provided with an ultraviolet light source that is used as a disinfectant for the user as well as the system. The system as disclosed in the instant invention includes at least one sensor unit provided therein to detect the presence and to identify the positioning of the vertical objects including human beings inside the system. Based on the input received from the sensor unit, the system is automatically switched ON/OFF. Further to this, the system includes an auxiliary positioning unit provided for the right positioning of vertical objects including patients, old age people and persons with limited motional ability inside the system. The system is additionally configured to shift the users after the completion of the washing and drying processes. The user of the system, in accordance with the most preferred embodiment of the instant invention, is enabled to control a plurality of attributes of the system and a display unit is adapted to display these pluralities of attributes of the functional elements of the system. The system is compact in size and configuration and is enabled with portability.

It is significant to note that the construction, arrangement, and functioning of the automatic system for providing full body shower to a user thereof as shown in the various exemplary embodiments are illustrative only. Although only a few preferred embodiments have been described in detail in the instant invention disclosure, those skilled in the pertinent art who review the instant invention disclosure will readily appreciate that many modifications are possible including variation in sizes, dimensions, structures, shapes and proportions of the various functional and structural elements, values of parameters, mounting arrangements, orientations, use of materials, colors and orientations, without actually departing from the novel teachings and advantages of the subject matter of the instant invention disclosure as described herein. The order or sequence of any process or method may be varied or re-sequenced according to alternative embodiments. Other substitutions, modifications, changes, and omissions may also be made in the design, operating conditions and arrangement of the various exemplary embodiments without departing from the scope and ambit of the instant invention as defined by the appended claims and equivalents thereof.

References herein to the position of elements like "top", "bottom", "above", "below" is merely used to describe the orientation of various structural and functional elements in the figures of the accompanying drawings. It should be noted herein that the orientation of various structural and functional elements may differ according to various embodiments, and that such variations are intended to encompass by the instant invention disclosure.

What is claimed is:

1. An automatic shower system for providing full body shower to a user, said system comprising:
   a solid supporting unit having a horizontal frame and a vertical frame wherein said horizontal frame extends from the top end of said vertical frame thereby making perpendicular orientation with respect to said vertical frame, the bottom end of said vertical frame mounted on to the ground using a mounting means;
   a marked region in front of said mounting means wherein said user is required to stand within the marked region to receive the full body shower wherein the presence of said user is detected by a sensor;
   at least one primary cleaning unit mounted onto said horizontal frame, said primary cleaning unit adapted to clean the head portion of said user;
   at least one secondary cleaning unit configured to be positioned in between said primary cleaning unit and said marked region, said secondary cleaning unit operably coupled to said vertical frame of said supporting unit via a ring arm, said secondary cleaning unit adapted to comprise plurality of uniform nozzles, brushes and a plurality of ultraviolet (UV) light sources;
   a first retractable water pipe cum brush located on the at least one secondary cleaning unit to clean face area or private area;
   a main control unit adapted to control the functioning of a plurality of functional elements of said system including a plurality of sensors; and
   a display unit adapted to display a plurality of attributes of said functional elements and enable said user to control said functional elements.

2. The automatic shower system of claim 1, wherein said secondary cleaning unit is selected from the group consisting of a circular, a semi-circular, an elliptical, a triangular, a square, a hexagonal and a tubular shape.

3. The automatic shower system of claim 1, wherein said secondary cleaning unit is configured to change its diameter.

4. The automatic shower system of claim 1, wherein the secondary cleaning unit is configured to include provision for multiple compartments or chambers to add soap, moisturizer or fragrance.

5. The automatic shower system of claim 1, wherein the secondary cleaning unit comprises a brush, said brush is configured to rotate circularly to rinse the whole body with help of a dedicated motor or using vertical movement of the secondary cleaning unit through a gear system.

6. The automatic shower system of claim 1, wherein the secondary cleaning unit comprises a brush cleaning chamber to clean the brush.

7. The automatic shower system of claim 6, wherein the brush is pulled by a motor in the brush cleaning chamber.

8. The automatic shower system of claim 6, wherein the brush is replaced by new brush in the brush cleaning chamber after the wash is over.

9. The automatic shower system of claim 1, wherein the brush is located at the end of a spring loaded arm or rods to adjust height of the brush in order to touch the body of the user.

10. The automatic shower system of claim 1, wherein the user has an option to insert a personalized or disposable brush to insert into a slot provided on the secondary cleaning unit, which after use is retracted to dispose.

11. The automatic shower system of claim 1, wherein the automatic shower system has a provision for wheelchair.

12. The automatic shower system of claim 1, wherein at least one supporting ring connected to the vertical frame is provided to support a disable person to enable the user to stand in upright position.

13. The automatic shower system of claim 1, wherein the automatic shower system comprises a cabinet to cover the automatic shower system.

14. The automatic shower system claim 13, wherein the cabinet comprises a button to automatically open a door of the cabinet.

15. The automatic shower system of claim 13, wherein the cabinet comprises an air ventilation unit to avoid build-up of moisture, fog or condensation.

16. The automatic shower system of claim 13, wherein the cabinet comprises an air conditioning unit to maintain temperature inside the cabinet.

17. The automatic shower system of claim 13, wherein the cabinet comprises an overhead water storage tank.

18. The automatic shower system of claim 13, wherein the cabinet comprises a blower to blow hot air through the floor of the cabinet to air dry the cabinet after completion of shower.

19. The automatic shower system of claim 13, wherein the cabinet is movable.

20. The automatic shower system of claim 13, wherein the cabinet is equipped with renewable energy sources.

* * * * *